United States Patent
Gabrilovich et al.

(10) Patent No.: US 11,073,521 B2
(45) Date of Patent: Jul. 27, 2021

(54) METHODS FOR MONITORING POLYMORPHONUCLEAR MYELOID DERIVED SUPPRESSOR CELLS

(71) Applicant: The Wistar Institute of Anatomy and Biology, Philadelphia, PA (US)

(72) Inventors: Dmitry I. Gabrilovich, Villanova, PA (US); Thomas C. Condamine, Philadelphia, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 301 days.

(21) Appl. No.: 15/577,922

(22) PCT Filed: May 31, 2016

(86) PCT No.: PCT/US2016/034993
§ 371 (c)(1),
(2) Date: Nov. 29, 2017

(87) PCT Pub. No.: WO2016/196451
PCT Pub. Date: Dec. 8, 2016

(65) Prior Publication Data
US 2018/0164313 A1    Jun. 14, 2018

Related U.S. Application Data

(60) Provisional application No. 62/187,991, filed on Jul. 2, 2015, provisional application No. 62/169,368, filed on Jun. 1, 2015.

(51) Int. Cl.
*G01N 33/569* (2006.01)
*G01N 33/574* (2006.01)
*C12N 5/0787* (2010.01)
*G01N 33/92* (2006.01)

(52) U.S. Cl.
CPC ..... *G01N 33/56972* (2013.01); *C12N 5/0642* (2013.01); *G01N 33/56977* (2013.01); *G01N 33/574* (2013.01); *G01N 33/57492* (2013.01); *G01N 33/92* (2013.01); *C12N 2503/00* (2013.01); *G01N 2333/705* (2013.01); *G01N 2333/70596* (2013.01)

(58) Field of Classification Search
CPC ....... G01N 33/56972; G01N 33/56977; G01N 33/574; G01N 33/57492; G01N 33/92; G01N 2333/705; G01N 2333/70596; C12N 5/0642; C12N 2503/00
See application file for complete search history.

(56) References Cited

U.S. PATENT DOCUMENTS

| | | |
|---|---|---|
| 6,573,102 B2 | 6/2003 | Li |
| 6,869,798 B2 | 3/2005 | Crews |
| 7,078,053 B2 | 7/2006 | Bunick |
| 2008/0267984 A1 | 10/2008 | Banchereau et al. |
| 2009/0203039 A1 | 8/2009 | Kominami et al. |
| 2012/0082688 A1 | 4/2012 | Chen et al. |
| 2014/0086869 A1 | 3/2014 | Rozenfeld |

FOREIGN PATENT DOCUMENTS

| | | |
|---|---|---|
| JP | 2010/105922 | 5/2010 |
| WO | WO 2015/200524 | 12/2015 |

OTHER PUBLICATIONS

Gielen et al. Increase in both CD14-positive and CD15-positive myeloid-derived suppressor cell subpopulations in the blood of patients with glioma but predominance of CD 15-positive myeloid-derived suppressor cells in glioma tissue. J Neuropathol Exp Neurol 74(5): 390-400, May 2015.*
Wu et al. T17 cells promote the accumulation and expansion of myeloid-derived suppressor cells in human colorectal cancer. Immunity 40: 785-800, May 15, 2014.*
Kim HR, et al., The Ratio of Peripheral Regulatory T Cells to Lox-1+ Polymorphonuclear Myeloid-derived Suppressor Cells Predicts the Early Response to Anti-PD-1 Therapy in Patients with Non-Small Cell Lung Cancer. Am J Respir Crit Care Med. 2019;199(2):243-246. doi:10.1164/rccm.201808-1502LE.
Condamine, T., et al., Lectin-type oxidized LDL receptor-1 distinguishes population of human polymorphonuclear myeloid-derived suppressor cells in cancer patients, *Sci. Immunol*, Aug. 2016, 1(2): doi:10.1126/sciimmunol.aaf8943.
Restriction Requirement dated Aug. 27, 2018 in related U.S. Appl. No. 15/668,867, filed Aug. 4, 2017.
Response to Restriction Requirement dated Oct. 26, 2018 in related U.S. Appl. No. 15/668,867, filed Aug. 4, 2017.
Non-Final Office Action dated Jan. 18, 2019 in related U.S. Appl. No. 15/668,867, filed Aug. 4, 2017.
Response to Non-Final Office Action dated Jul. 18, 2019 in related U.S. Appl. No. 15/668,867, filed Aug. 4, 2017.
Final Office Action dated Aug. 29, 2019 in related U.S. Appl. No. 15/668,867, filed Aug. 4, 2017.
Response to Final Office Action dated Nov. 27, 2019 in related U.S. Appl. No. 15/668,867, filed Aug. 4, 2017.
Advisory Action dated Dec. 9, 2019 in related U.S. Appl. No. 15/668,867, filed Aug. 4, 2017.
Response to Advisory Action dated Feb. 20, 2020 in related U.S. Appl. No. 15/668,867, filed Aug. 4, 2017.

(Continued)

*Primary Examiner* — Alana Harris Dent
(74) *Attorney, Agent, or Firm* — Howson and Howson LLP; Mary E. Bak

(57) ABSTRACT

A method of obtaining a population of cells enriched in human polymorphonuclear myeloid derived suppressor cells (PMN-MDSCs) comprises isolating from a cell suspension those cells which express LOX-1 to provide a population of cells enriched with PMN-MDSCs. A method of monitoring the population of LOX-1+ cells in a cell-containing biological sample is useful for determining the efficacy of treatment or the metastasis or increasing progression of cancer. Other cell isolation and diagnostic methods are also described.

9 Claims, 9 Drawing Sheets

(56) References Cited

OTHER PUBLICATIONS

Final Office Action dated Mar. 30, 2020 in related U.S. Appl. No. 15/668,867, filed Aug. 4, 2017.
Pillay, J. et al., Immune suppression by neutrophils and granulocytic myeloid-derived suppressor cells: similarities and differences, Cellular and Molecular Life Sciences, Feb. 2013, 70:3813-3827.
Dumitru, C. A. et al., Neutrophils and granulocytic myeloid-derived suppressor cells: immunophenotyping, cell biology and clinical relevance in human oncology, Cancer Immunology Immunotherapy, Jun. 2012, 61:1155-1167.
Zhao, F. et al., S100A9 a new marker for monocytic human myeloid-derived suppressor cells, Immunology, Jun. 2012, 136(2):176-183.
Wu, Zhuang, et al., LOX-1 Deletion Improves Neutrophil Responses, Enhances Bacterial Clearance, and Reduces Lung Injury in a Murine Polymicrobial Sepsis Model $^\nabla$, Infection and Immunity, Jul. 2011, 79(7):2865-2870.
Yang, W. C. et al., Polarization and reprogramming of myeloid-derived suppressor cells, Journal of Molecular Cell Biology, Apr. 2013, 0:1-3.
International Search Report dated Aug. 30, 2016 in corresponding International Patent Application No. PCT/US16/34993, filed May 31, 2016.
Written Opinion dated Aug. 30, 2016 in corresponding International Patent Application No. PCT/US16/34993, filed May 31, 2016.
Al-Banna, N. and Lehmann, C., Oxidized LDL and LOX-1 in experimental sepsis, Mediators of Inflammation, Aug. 2013, article ID: A761789, 6 pages.
Bettigole, S. E. and Glimcher, L. H., Endoplasmic Reticulum Stress in Immunity, Annual Review of Immunology, Dec. 2014, 33:107-38.
Claudio, N. et al, Mapping the crossroads of immune activation and cellular stress response pathways, The EMBO Journal, Apr. 2013, 32:1214-24.
Condamine, T. et al., Transcriptional regulation of myeloid-derived suppressor cells, The Journal of Leukocyte Biology, Dec. 2015, 98(6):913-22.
Condamine, T. et al., ER stress regulates myeloid-derived suppressor cell fate through TRAIL-R-mediated apoptosis, The Journal of Clinical Investigation, Jun. 2014, 124(6):2626-39.
Condamine, T. et al., Regulation of tumor metastasis by myeloid-derived suppressor cells, Annual Review of Medicine, Jan. 2015, 66:97-110.
De Siqueira, J. et al., Clinical and Preclinical Use of LOX-1-Specific Antibodies in Diagnostics and Therapeutics, Journal of Cardiovascular Translational Research, Nov. 2015, 8(8):458-65.
Diaz-Montero, C. M. et al., Increased circulating myeloid-derived suppressor cells correlate with clinical cancer stage, metastatic tumor burden, and doxorubicin-cyclophosphamide chemotherapy, Cancer Immunology Immunotherapy, Jan. 2009, 58(1):49-59.
Condamine, T. et al., Aug. 2016, Lectin-type oxidized LDL receptor-1 distinguishes population of human polymorphonuclear myeloid-derived supporessor cells in cancer patients. Sci. Immunol., 1(2):doi:10.1126/sciimmunol.aaf8943.
Feng, P. H. et al., CD14(+)S100A9(+) monocytic myeloid-derived suppressor cells and their clinical relevance in non-small cell lung cancer, American Journal of Respiratory and Critical Care Medicine, Nov. 2012, 186(10):1025-36.
Filipazzi, P. et al., Identification of a new subset of myeloid suppressor cells in peripheral blood of melanoma patients with modulation by a granulocyte-macrophage colony-stimulation factor-based antitumor vaccine, Journal of Clinical Oncology, Jun. 2007, 25(18):2546-53.
Finke, J. et al., MDSC as a mechanism of tumor escape from sunitinib mediated anti-angiogenic therapy, International Immunopharmacology, Jul. 2011, 11(7):853-8.
Finkelstein, S. E. et al., Changes in dendritic cell phenotype after a new high-dose weekly schedule of interleukin-2 therapy for kidney cancer and melanoma, Journal of Immunotherapy, Oct. 2010, 33:817-27.

Fridlender, Z. G. et al., Transcriptomic analysis comparing tumor-associated neutrophils with granulocytic myeloid-derived suppressor cells and normal neutrophils, PLoS One, Feb. 2012, 7(2):e31524.
Gabrilovich, D. I. and Nagaraj, S., Myeloid-derived suppressor cells as regulators of the immune system, Nature Reviews Immunology, Mar. 2009, 9(3):162-174.
Gabrilovich, D. I. et al., Coordinated regulation of myeloid cells by tumours, Nature Reviews Immunology, Apr. 2012, 12(4):253-68.
Hirsch, H. A. et al., A transcriptional signature and common gene networks link cancer with lipid metabolism and diverse human diseases, Apr. 2010, Cancer Cell, 17:348-61.
Holcik, M. and Sonenberg, N., Translational control in stress and apoptosis, Nature Reviews Molecular Cell Biology, Apr. 2005, 6(4):318-27.
Hong, D. et al., High-Density Lipoprotein Prevents Endoplasmic Reticulum Stress-Induced Downregulation of Liver LOX-1 Expression: e0124285, PloS One, Apr. 2015, 10(4):1-12.
Hong, D. et al., Ox-LDL induces endothelial cell apoptosis via the LOX-1-dependent endoplasmic reticulum stress pathway, Atherosclerosis, Aug. 2014, 235(2):310-7.
Kimura, T. et al., MUC1 vaccine for individuals with advanced adenoma of the colon: a cancer immunoprevention feasibility study, Cancer Prevention Research, Jan. 2013, 6(1):18-26.
Kumar, V. et al., The nature of myeloid-derived suppressor cells in the tumor microenvironment, Trends in Immunology, Mar. 2016, 37(3):208-20.
Lee, B. R. et al., Elevated endoplasmic reticulum stress reinforced immunosuppression in the tumor microenvironment via myeloid-derived suppressor cells, Oncotarget, Dec. 2014, 5(23):12331-45.
Liu, C. Y. et al., Population alterations of L-arginase- and inducible nitric oxide synthase-expressed CD11b+/CD14(−)/CD15+/CD33+ myeloid-derived suppressor cells and CD8+ T lymphocytes in patients with advanced-stage non-small cell lung cancer, Journal of Cancer Research and Clinical Oncology, Jan. 2010, 136(1):35-45.
Lu, J. et al., Oxidative stress and lectin-like ox-LDL-receptor LOX-1 in atherogenesis and tumorigenesis, Antiox Redox Signal, Oct. 2011, 15(8):2301-33.
Mandruzzato, S. et al., Toward harmonized phenotyping of human myeloid derived suppressor cells by flow cytometry: results from an interim study, Cancer Immunol Immunother, Feb. 2016, 65(2):161-9.
Marvel, D and Gabrilovich, D. I., Myeloid-derived suppressor cells in the tumor microenvironment: expect the unexpected, J Clin Invest, Sep. 2015, 125(9):3356-64.
Mehadevan, N. R. and Zanetti, M., Tumor stress inside out: cell-extrinsic effects of the unfolded protein response in tumor cells modulate the immunological landscape of the tumor microenvironment, J Immunol, Nov. 2011, 187(9):4403-9.
Mehadevan, N. R. et al., Cell-extrinsic effects of tumor ER stress imprint myeloid dendritic cells and impair CD8$^+$ T cell priming, PLoS One, Dec. 2012, 7(12):e51845.
Mehadevan, N. R. et al., Transmission of endoplasmic reticulum stress and pro-inflammation from tumor cells to myeloid cells, Proc Natl Acad Sci USA, Apr. 2011, 108(16):6561-6.
Mehta, J. L. et al., LOX-1: a new target for therapy for cardiovascular diseases, Cardiovasc Drugs Ther, Oct. 2011, 25(5):495-500.
Mehta, J. L. et al., Deletion of LOX-1 reduces atherogenesis in LDLR knockout mice fed high cholesterol diet, Circ Res, Jun. 2007, 100(11):1634-42.
Messmer, M. N. et al., Tumor-induced myeloid dysfunction and its implications for cancer immunotherapy, Cancer Immunol Immunother, Jan. 2015, 64(1):1-13.
Meyer, C. et al., Frequencies of circulating MDSC correlate with clinical outcome of melanoma patients treated with ipilimumab, Canc Immunol Immunother, Mar. 2014, 63(3):247-57.
Montero, A. J. et al., Myeloid-derived suppressor cells in cancer patients: a clinical perspective, J Immunother, Feb. 2012, 35(2):107-15.
Nelson, A. L., Antibody Fragments: Hope and Hype, MAbs, Jan. 2010, 2(1):77-83.
Zhang, K. and Kaufman, R. J., From endoplasmic-reticulum stress to the inflammatory response, Nature, Jul. 2008, 454(7203):455-62.

(56) References Cited

OTHER PUBLICATIONS

Pirillo, A. et al., LOX-1, OxLDL, and atherosclerosis, Mediators Inflamm, Jul. 2013, 152:786.

Poschke, I. et al., On the armament and appearances of human myeloid derived suppressor cells, Clin Immunol, Sep. 2012, 144(3):250-68.

Ramachandran, I. R. et al., Myeloid-derived suppressor cells regulate growth of multiple myeloma by inhibiting T cells in bone marrow, J Immunol, Apr. 2013, 190(7):3815-23.

Ron, D. and Walter, P., Signal integration in the endoplasmic reticulum unfolded protein response, Nat Rev Mol Cell Biol, Jul. 2007, 8(7):519-29.

Sawamura, A. et al., LOX-1: a multiligand receptor at the crossroads of response to danger signals, Curr Opin Lipidol, Oct. 2012, 23(5):439-45.

Sawamura, T. et al., An endothelial receptor for oxidized low-density lipoprotein, Nature, Mar. 1997, 386(6620):73-7.

Storey, J.D. and Tibshirani, R., Statistical significance for genomewide studies, Proc Natl Acad Sci USA, Aug. 2003, 100(16):9440-5.

Talmadge, J. E. and Gabrilovich, D. I., History of myeloid-derived suppressor cells, Nat Rev Cancer, Oct. 2013, 13(10):739-52.

Tang, C. H. et al., Inhibition of ER stress-associated IRE-1/XBP-1 pathway reduces leukemic cell survival, J Clin Invest, Jun. 2014, 124(6):2585-98.

Tarhini, A. A. et al., Immune monitoring of the circulation and the tumor microenvironment in patients with regionally advanced melanoma receiving neoadjuvant ipilimumab, PLoS One, Feb. 2014, 9(2):e87705.

Taye, A. and El-Sheikh, A. A., Lectin-like oxidized low-density lipoprotein receptor 1 pathways, Eur J Clin Invest, Jul. 2013, 43(7):740-5.

Thevenot, P. T. et al., The stress-response sensor chop regulates the function and accumulation of myeloid-derived suppressor cells in tumors, Immunity, Sep. 2014, 41(3):389-401.

Vetsika, E. K. et al., A circulating subpopulation of monocytic myeloid-derived suppressor cells as an independent prognostic/predictive factor in untreated non-small lung cancer patients, J Immunol Res, Nov. 2014, 65:92-4.

Walter, P. and Ron D., The unfolded protein response: from stress pathway to homeostatic regulation, Science, 2011, Nov. 2011, 334(6059):1081-6.

Wang, X. et al., LOX-1 and angiotensin receptors, and their interplay, Cardiovasc Drugs Ther, Oct. 2011, 25(5):401-17.

Wang, Z. et al., Association of myeloid-derived suppressor cells and efficacy of cytokine-induced killer cell immunotherapy in metastatic renal cell carcinoma patients, J Immunother, Jan. 2014, 37(1):43-50.

Zhang, S., A comprehensive evaluation of SAM, the SAM R-package and a simple modification to improve its performance, BMC bioinformatics, Jun. 2007, 8:230.

Yoshimoto, R. et al., The discovery of LOX-1, its ligands and clinical significance, Cardiovasc Drugs Ther, Oct. 2011, 25(5):379-91.

Youn, J. I. et al., Subsets of myeloid-derived suppressor cells in tumor-bearing mice, J Immunol, Oct. 2008, 181(8):5791-802.

Youn, J. I. et al., Characterization of the nature of granulocytic myeloid-derived suppressor cells in tumor-bearing mice, J Leukoc Biol, Jan. 2012, 91(1):167-81.

\* cited by examiner

FIG. 4A
FIG. 4B
Proportion of CD11b$^+$ CD33$^+$ CD14$^-$ CD15$^+$ LOX1$^+$ cells among all leukocytes
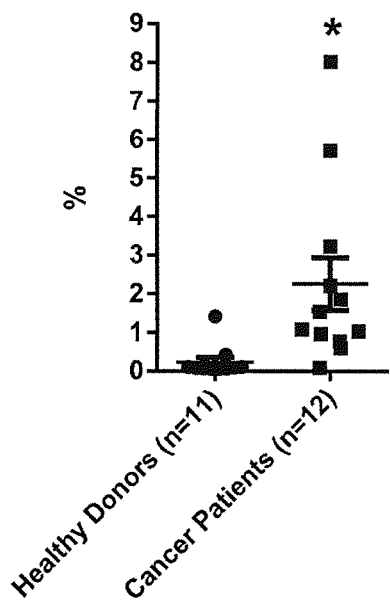
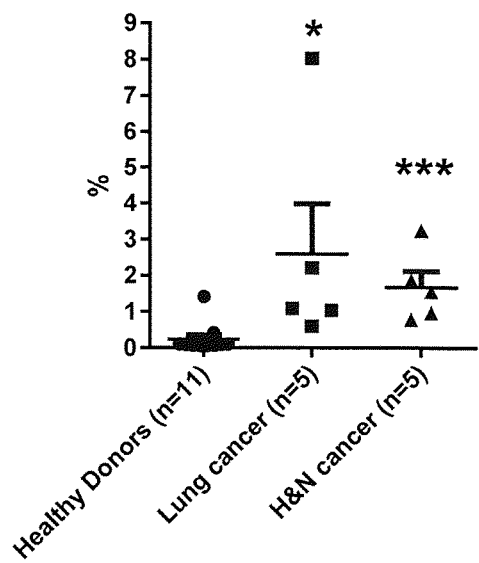

FIG. 4C
FIG. 4D
Proportion of Lox1$^+$ cells among neutrophils (CD11b$^+$ CD33$^+$ CD15$^+$ CD14$^-$)
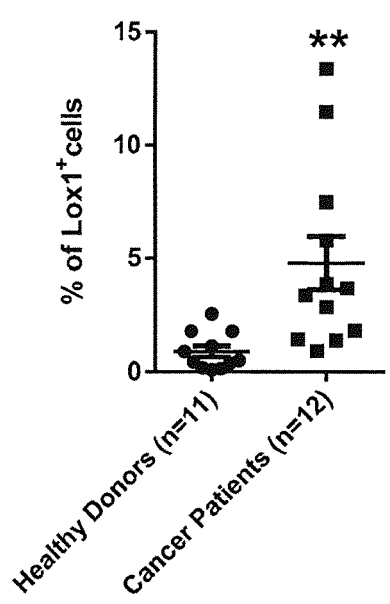
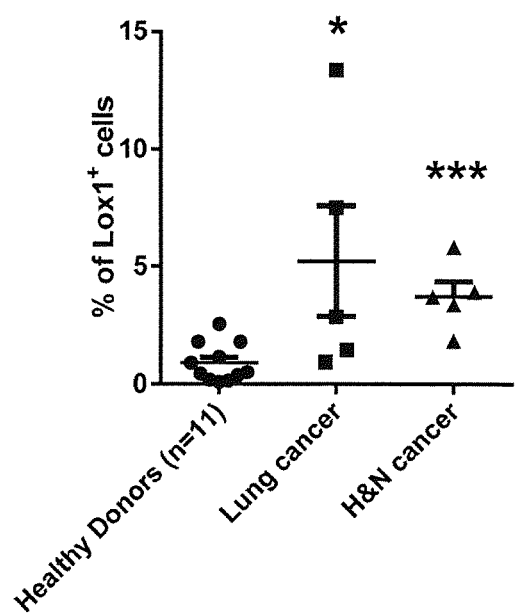

patient 15-09 - Head and Neck - late stage
FIG. 6A   No Stimulation   FIG. 6B
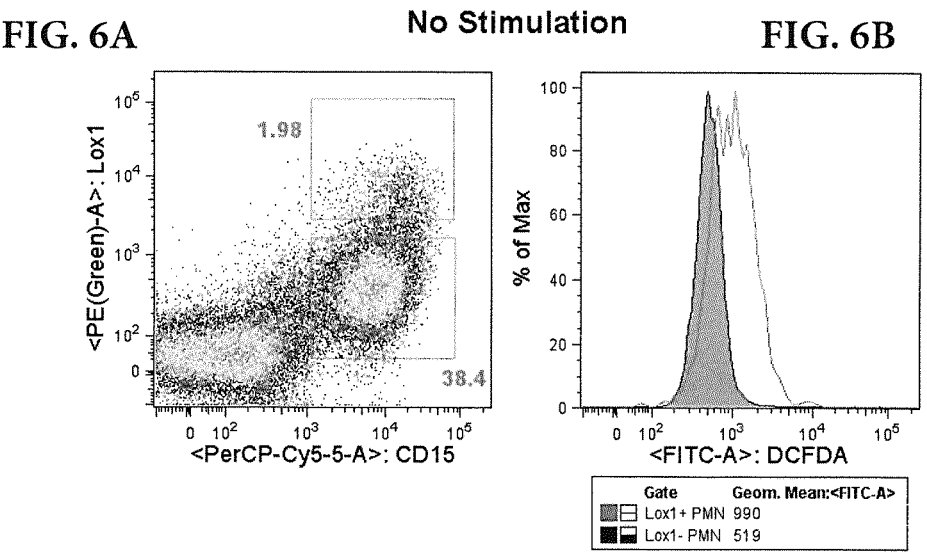
patient 15-14 - Head and Neck - late stage
FIG. 6C   No Stimulation   FIG. 6D
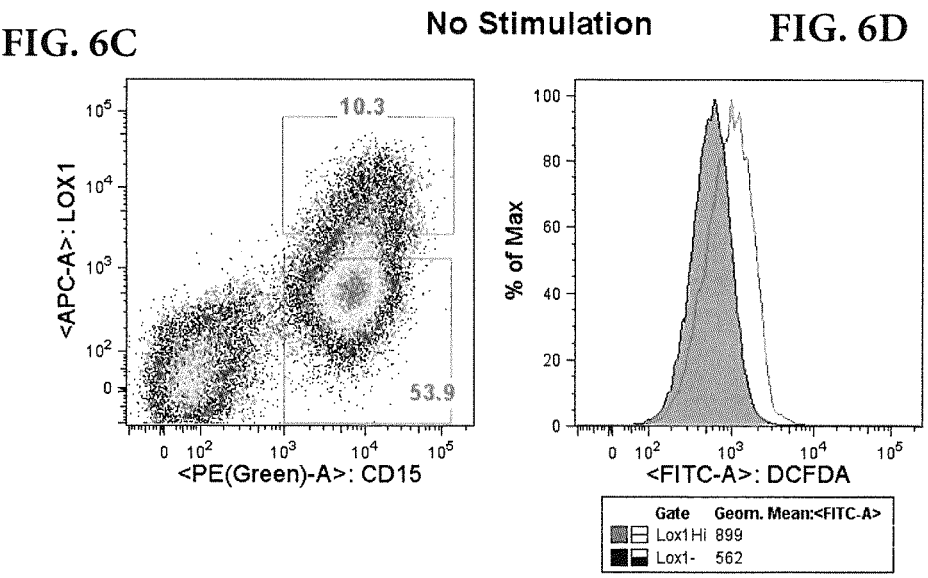

Lung Cancer Serum

Colon Cancer Serum

METHODS FOR MONITORING POLYMORPHONUCLEAR MYELOID DERIVED SUPPRESSOR CELLS

CROSS-REFERENCE TO RELATED APPLICATIONS

This application is a 371 of International patent application No. PCT/US2016/034993, filed May 31, 2016, which claims the benefit of the priority U.S. Provisional Patent Applications No. 62/187,991 filed Jul. 2, 2015 and No. 62/169,368, filed Jun. 1, 2015, which applications are incorporated by reference herein.

BACKGROUND OF THE INVENTION

Myeloid-derived suppressor cells (MDSC) represent a heterogeneous population of immature myeloid cells. These cells accumulate to a great extent in cancer patients and play a major role in regulating immune responses in cancer[1]. MDSC suppress T cells activation and proliferation as well as function of natural killer (NK) cells[2,3]. Ample evidence links these cells with tumor progression and outcome of the disease in cancer patients[4,5]. MDSC have been divided in two different sub-populations[6], monocytic myeloid-derived suppressor cells (M-MDSC) and polymorphonuclear myeloid-derived suppressor cells (PMN-MDSC). About 20-30% of MDSC consists of monocytic cells, i.e., M-MDSC, and are generally associated with high activity of Arginase-1 and iNOS[7]. Two different phenotypes ($CD11b^+$ $CD14^-$ $CD15^-$ and $CD33^+$ or $CD11b^+$ $CD14^+$ $CD33^+$ and) $HLA-DR^{lo}$ are used to characterize these M-MDSC cells depending on the type of cancer. The second population, i.e., PMN-MDSC, are comprised of granulocytic cells and are usually associated with high level of ROS production[8]. PMN-MDSC represent the major population of MDSC (about 60-80%) and are characterized as $CD11b^+$ $CD14^-$ $CD15^+$ and $CD33^+$.

One of the major obstacles in the identification of PMN-MDSC is that they share the same phenotype with normal polymorphonuclear cells (PMN). Current methods for separating populations of PMN-MDSC from populations of PMN in biological fluids are complicated, time-consuming and inaccurate, requiring multiple gradient separation as well as multi-color flow cytometry analysis. Normal PMN have high density and pass through the gradient, whereas PMN-MDSC have lower density become trapped on the gradient together with mononuclear cells. This process of distinguishing between the two sets of PMN has two major shortcomings.

The density of the cells depends on many parameters, such as conditions for collection, time of storage, etc., which affect the proportion of the cells obtained on the gradient regardless of their PMN-MDSC true state. These conditions thus introduce errors into the analysis. Additionally, these processes are inconvenient and difficult to standardize. Thus, there are no useful methods currently exist that allow for discrimination of these two populations in blood and tissues.

SUMMARY OF THE INVENTION

In one aspect, a method for monitoring the population of polymorphonuclear myeloid derived suppressor cells (PMN-MDSCs) in a mammalian subject involves contacting a biological fluid sample from the subject containing polymorphonuclear neutrophils (PMNs) and PMN-MDSC with a ligand that specifically binds or forms a complex with LOX-1 on the cell surface. Detecting and distinguishing the complexes of ligand-bound LOX-1-cells from other cells not bound to the ligand in the sample enables the tracking of the number or changes in the number of PMN-MDSCs substantially free of PMN.

In another aspect a method of differentiating polymorphonuclear myeloid derived suppressor cells (PMN-MDSCs) from polymorphonuclear neutrophils (PMNs) in a biological sample containing both types of cells involves contacting the sample with a ligand that specifically binds or forms a complex with LOX-1 on the cell surface. The LOX-1-bound cells can be detected, identified or measured apart from other cells not bound to the ligand in the sample. The LOX-1-bound cells are PMN-MDSCs substantially free of PMN.

In another aspect, a method of obtaining a population of PMN-MDSC from a biological sample containing other cell types comprises isolating from a cell suspension those cells which express LOX-1 to provide a population of cells enriched with PMN-MDSCs.

In another aspect, a method for differential diagnosis of cancer comprises contacting a biological sample of a subject with reagents capable of complexing or binding with LOX-1 on the surface of a cell; and detecting or measuring any cells that complex with the reagent. Cells that form a complex with the LOX-1 reagent indicate the presence of cancer cells in the sample.

A substantially pure population of PMN-DMSCs produced by isolating $LOX-1^+$ cells from a biological sample by contacting the sample with a reagent that forms a complex or binds to LOX-1.

Other aspects and advantages of these compositions and methods are described further in the following detailed description of the preferred embodiments thereof.

BRIEF DESCRIPTION OF THE DRAWINGS

FIG. 4A is a graph showing the proportion of LOX-1⁺ CD11b⁺, CD33⁺, CD14⁻, CD15⁺ cells (neutrophils) among all leukocytes in unseparated whole blood. Samples of whole blood were collected from 11 healthy donors (●) and 12 cancer patients (■), lung cancer and head and neck cancer. Red cells were lysed and the rest evaluated directly by flow cytometry.

FIG. 4B is a graph showing the proportion of LOX-1⁺ CD11b⁺, CD33⁺, CD14⁻, CD15⁺ cells (neutrophils) among all leukocytes in unseparated whole blood. Samples of whole blood were collected from 11 healthy donors (●), 5 lung cancer patients (■), and 5 head and neck cancer patients (H&N, ▲). Red cells were lysed and the rest evaluated directly by flow cytometry. *-p<0.05; ***-p<0.001.

FIG. 4C is a graph showing the proportion of LOX-1⁺ CD11b⁺, CD33⁺, CD14⁻, CD15⁺ cells among all neutrophils in unseparated whole blood. Samples of whole blood were collected from 11 healthy donors (●) and 12 cancer patients (■). Red cells were lysed and the rest evaluated directly by flow cytometry. **-p<0.01.

FIG. 4D is a graph showing the proportion of LOX-1⁺ CD11b⁺, CD33⁺, CD14⁻, CD15⁺ cells among all neutrophils in unseparated whole blood. Samples of whole blood were collected from 11 healthy donors (●), lung cancer (■) and head and neck cancer (▲) patients. Red cells were lysed and the rest evaluated directly by flow cytometry. *-p<0.05; ***-p<0.001.

FIG. 6A is a histogram showing ROS in PMN from head and neck cancer patient No. 15-09. Samples of whole blood were collected. Red cells were lysed and PMN were labeled with CD15, LOX-1 antibodies and DCFDA (to measure ROS). FIG. 6A shows the gating strategy of CD15⁺LOX-1⁺ or LOX-1⁻ cells. Mean fluorescence intensity is shown under the histogram.

FIG. 6B is a histogram from patient No. 15-09 showing the intensity of DCFDA fluorescence reflecting the amount of ROS. Mean fluorescence intensity is shown under the histogram.

FIG. 6C is a histogram showing ROS in PMN from head and neck cancer patient No. 15-14. PMN were obtained and labeled as in FIG. 6A. FIG. 6 C shows the gating strategy of CD15⁺LOX-1⁺ or LOX-1⁻ cells. Mean fluorescence intensity is shown under the histogram.

FIG. 6D is a histogram from patient No. 15-14 showing the intensity of DCFDA fluorescence reflecting the amount of ROS. Mean fluorescence intensity is shown under the histogram.

DETAILED DESCRIPTION OF THE INVENTION

Figure 1:
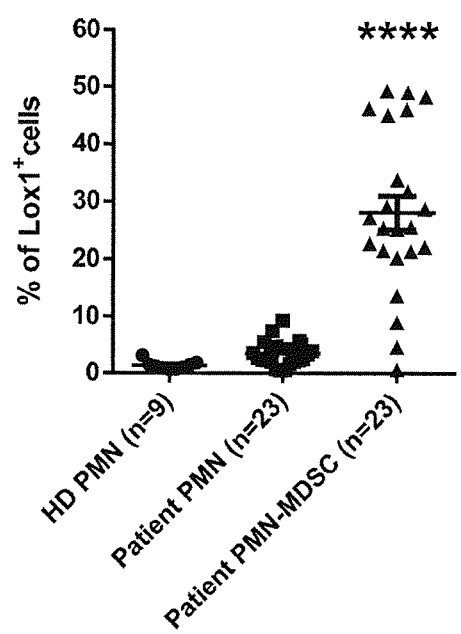
FIG. 1 is a graph showing the proportion of LOX-1 positive cells among $CD11b^+CD14^-CD33^+CD15^+$ polymorphonuclear cells (PMN) and PMN-MDSC in 23 cancer patients (PMN, ■; and PMN-MDSC, ▲) and PMN in 9 healthy donors (HD, ●). Peripheral blood was subjected to gradient centrifugation using Ficcol and Percoll gradients. PMN-MDSC are evaluated in mononuclear fraction and PMN in granulocytic fraction as described in the text. The proportion of LOX-1 positive cells was evaluated by flow cytometry. ****-$p<0.0001$ between patients PMN-MDSC and PMN.
Figure 2A:
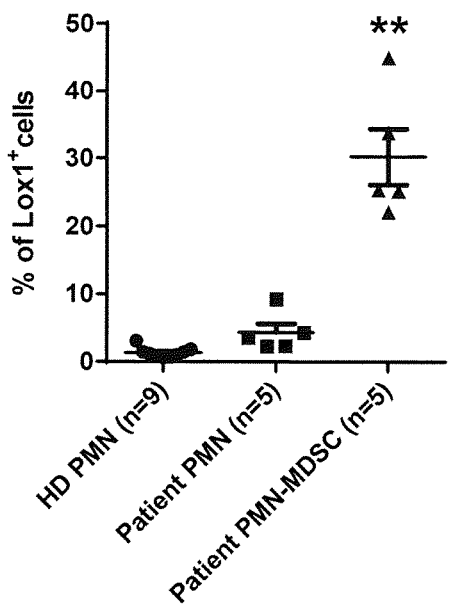
FIG. 2A is a graph showing the percentage of LOX-1 positive cells among $CD11b^+CD14^-CD33^+CD15^+$ PMN (■) and PMN-MDSC (▲) in 5 head and neck cancer patients and PMN (●) in 9 healthy donors (HD). The data is shown as in FIG. 1 but separated based on the cancer types. **-$p<0.01$ between patients PMN-MDSC and PMN.
Figure 2B:
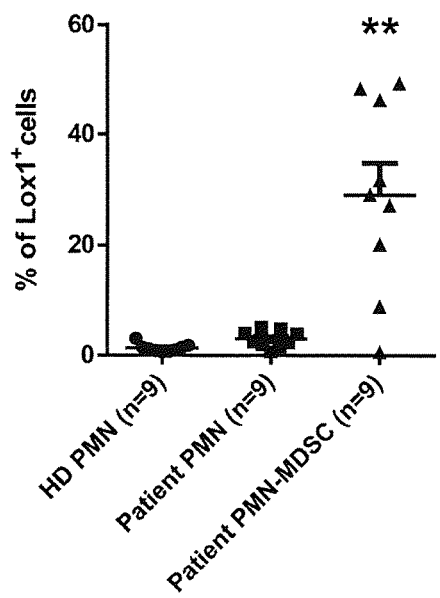
FIG. 2B is a graph showing the percentage of LOX-1 positive cells among $CD11b^+CD14^-CD33^+CD15^+$ PNM (■) and PMN-MDSC (▲) in 9 lung cancer patients and PMN (●) in 9 healthy donors (HD). The data is shown as in FIG. 1 but separated based on the cancer types. **-$p<0.01$ between patients PMN-MDSC and PMN.
Figure 2C:
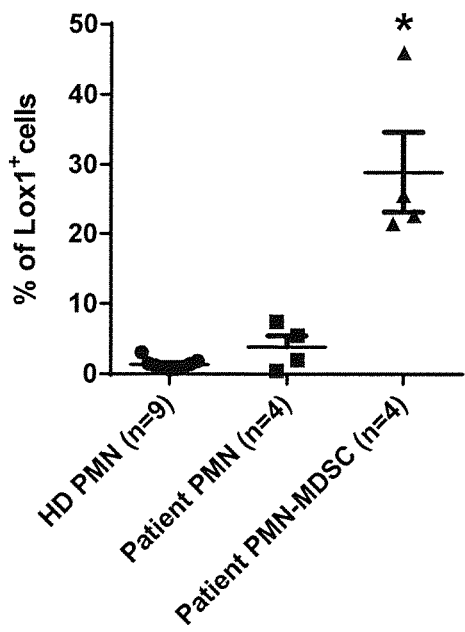
FIG. 2C is a graph showing the percentage of LOX-1 positive cells among $CD11b^+CD14^-CD33^+CD15^+$ PNM (■) and PMN-MDSC (▲) in 4 colon cancer patients, and PMN (●) in 9 healthy donors. The data is shown as in FIG. 1 but separated based on the cancer types. *-$p<0.05$ between patients PMN-MDSC and PMN.
Figure 2D:
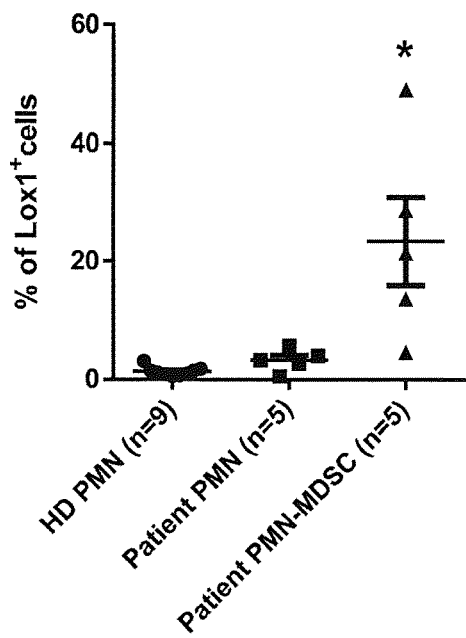
FIG. 2D is a graph showing the percentage of LOX-1 positive cells among CD11b⁺CD14⁻CD33⁺CD15⁺ PNM (■) and PMN-MDSC (▲) in 5 breast cancer patients and PMN (●) in 9 healthy donors. The data is shown as in FIG. 1 but separated based on the cancer types. *-p<0.05 between patients PMN-MDSC and PMN.

As disclosed herein, methods and compositions are described which are useful in the isolation of certain cells indicative of cancer in a mammalian subject. Cell preparations that are substantially purified PMN-DMSCs are prepared by methods involving the use of reagents that complex with or bind the LOX-1 biomarker on the surface of cells, thereby discriminating between PMN cells and PMN-DMSCs. The methods described herein are also useful for the diagnosis and/or monitoring of cancer and tumor cells, i.e., both malignant and benign tumors, so long as the cells to be treated carry the LOX-1 cell surface antigen.

Definitions and Components of the Methods

Unless defined otherwise in this specification, technical and scientific terms used herein have the same meaning as commonly understood by one of ordinary skill in the fields of biology, biotechnology and molecular biology and by reference to published texts, which provide one skilled in the art with a general guide to many of the terms used in the present application. The definitions herein are provided for clarity only and are not intended to limit the claimed invention.

"Patient" or "subject" as used herein means a mammalian animal, including a human, a veterinary or farm animal, a domestic animal or pet, and animals normally used for clinical research. In one embodiment, the subject of these methods and compositions is a human.

The term "LOX-1" as used herein is a cell surface receptor, oxidized low density lipoprotein (lectin-like) receptor 1, first identified in endothelial cells as one of the main receptors for oxidized-LDL (ox-LDL)[10]. Besides ox-LDL, this receptor has been shown to bind many different ligands including other modified lipoproteins, advanced glycosylation end products, aged red blood cells, apoptotic cells and activated platelets". Interestingly LOX-1 has been involved in many different pathological conditions including atherogenesis, myocardial ischemia, hypertension, vascular diseases and thrombosis". Expression of LOX-1 can be induced by a wide array of stimuli including pro-inflammatory factor (TNF-α, IL-1β or IFN-γ), angiotensin II, endothelin-1, modified lipoproteins and free radicals[12]. Engagement of LOX-1 can lead to induction of oxidative stress, apoptosis, endothelial dysfunction, fibrosis and inflammation through the activation of the NF-κB pathway. LOX-1 has also been described to play a role in tumorigenesis[13]. Indeed, LOX-1 up-regulation has been observed during cellular transformation into cancer cell and can have a pro-oncogenic effect by activating the NF-κB pathway, by increasing DNA damage through increase ROS production and by promoting angiogenesis and cell dissemination[13,14]. The nucleic acid sequence for the gene encoding LOX-1 (gene name OLR1) can be found in databases such as NCBI, i.e., NCBI gene ID: 4973 or Gene sequence: Ensembl: ENSG00000173391. The LOX-1 protein sequence is found at Hugo Gene Nomenclature Committee 8133, Protein Sequence HPRD:04003. It should be understood that the term LOX-1 can also represent the receptor protein in various species, and with conservative changes in the amino acid or encoding sequences, or with other naturally occurring modifications that may vary among species and between members of the same species, as well as naturally occurring mutations thereof.

The term "cancer" or "tumor" as used herein refers to, without limitation, refers to or describes the physiological condition in mammals that is typically characterized by unregulated cell growth. By cancer as used herein is meant any form of cancer, including hematological cancers, e.g., leukemia, lymphoma, myeloma, bone marrow cancer, and epithelial cancers, including, without limitation, breast cancer, lung cancer, prostate cancer, colorectal cancer, brain cancer, endometrial cancer, esophageal cancer, stomach cancer, bladder cancer, kidney cancer, pancreatic cancer, cervical cancer, head and neck cancer, ovarian cancer, melanoma, leukemia, myeloma, lymphoma, glioma, Non-Hodgkin's lymphoma, leukemia, multiple myeloma and multidrug resistant cancer. A "tumor" is an abnormal mass of tissue that results from excessive cell division that is uncontrolled and progressive, and is also referred to as a neoplasm. The term "tumor," as used herein, refers to all neoplastic cell growth and proliferation, whether malignant or benign, and all pre-cancerous and cancerous cells and tissues. Whenever the term "lung cancer" is used herein, it is used as a representative cancer for demonstration of the use of the methods and compositions described herein.

"Sample" as used herein means any biological fluid or suspension or tissue from a subject that contains cells carrying the LOX-1+ biomarker or cell surface antigen identified herein. The sample in one embodiment contains cells that are both PMN and PMN-MDSC. The sample in one embodiment contains cells carrying one or more other biomarkers or cell surface antigens indicative of polymorphonuclear cells or neutrophils. In one embodiment, cells (neutrophils) in the sample express CD66b+. In another embodiment, cells (neutrophils) in the sample express CD15+. In still another embodiment, cells in the sample express CD11b+ or CD33+. The most suitable samples for use in the methods and with the diagnostic compositions or reagents described herein are fluid samples or suspensions which require minimal invasion for testing, e.g., blood samples, including whole blood, and any fluids containing shed or circulating tumor cells. It is anticipated that other biological fluids that contain cells at a sufficiently detectable concentration, such as peripheral blood, serum, saliva or urine, vaginal or cervical secretions, and ascites fluids or peritoneal fluid may be similarly evaluated by the methods described herein. In one embodiment, the sample is a tumor secretome, i.e., any fluid or medium containing the proteins secreted from the tumor. These shed proteins may be unassociated, associated with other biological molecules, or enclosed in a lipid membrane such as an exosome. Also, circulating tumor cells or fluids containing them are also suitable samples for evaluation in certain embodiments of this invention. In another embodiment, the biological sample is a tissue or tissue extract containing the PMN-MDSC. In one embodiment, such samples may further be diluted with or suspended in, saline, buffer or a physiologically acceptable diluent. Alternatively, such samples are tested neat. In another embodiment, the samples are concentrated by conventional means.

The term "biomarker" as described in this specification includes any physiological molecular form, or modified physiological molecular form, isoform, pro-form, naturally occurring forms or naturally occurring mutated forms of LOX-1 and peptide fragments of LOX-1, expressed on the cell surface, unless otherwise specified. Other biomarkers that may be useful to detect neutrophils to assist in distinguishing the two subsets PMN and PMN-MCSCs according to the teachings herein include CD66b, CD11b, CD33, CD15 and/or CD14. It is understood that all molecular forms useful in this context are physiological, e.g., naturally occurring in the species. Preferably the peptide fragments obtained from the biomarkers are unique sequences. However, it is understood that other unique fragments may be obtained readily by one of skill in the art in view of the teachings provided herein.

By "isoform" or "multiple molecular form" is meant an alternative expression product or variant of a single gene in a given species, including forms generated by alternative splicing, single nucleotide polymorphisms, alternative promoter usage, alternative translation initiation small genetic differences between alleles of the same gene, and posttranslational modifications (PTMs) of these sequences.

By "related proteins" or "proteins of the same family" are meant expression products of different genes or related genes identified as belonging to a common family. Related proteins in the same biomarker family, e.g., LOX-1, may or may not share related functions. Related proteins can be readily identified as having significant sequence identity either over the entire protein or a significant part of the protein that is typically referred to as a "domain"; typically proteins with at least 20% sequence homology or sequence identity can be readily identified as belonging to the same protein family.

By "homologous protein" is meant an alternative form of a related protein produced from a related gene having a percent sequence similarity or identity of greater than 20%, greater than 30%, greater than 40%, greater than 50%, greater than 60%, greater than 70%, greater than 75%, greater than 80%, greater than 85%, greater than 90%, greater than 95%, greater than 97%, or greater than 99%.

The term "ligand" with regard to protein biomarkers refers to a molecule that binds or complexes, with the PMN-MDSC biomarker protein, e.g., LOX-1. Thus, a ligand can be an amino acid sequence or protein sequence, or a molecular form or peptide, such as an antibody, antibody mimic or equivalent, or a fragment thereof. The ligand can be a naturally occurring peptide that binds to a portion of the LOX-1 receptor or a synthetically or recombinantly produced chimeric peptide having a portion that binds to the LOX-1 receptor and a portion designed for other purposes, e.g., to assist in the detection of the binding. Similarly the peptide may be designed, or a small molecule designed, to bind to LOX-1 by mimicking the three-dimensional physical structure of the LOX-1 receptor. The term ligand as used with respect to the neutrophil biomarkers, e.g., CD15 and CD66b, refers to similar amino acid sequences, peptides, chimeric proteins, etc, which can bind with the respective cell surface receptor CD15 or CD66b.

The term "ligand" with regarding to a nucleic acid sequence encoding a biomarker, refers to a molecule that binds or complexes, with the indicated biomarker nucleic acid, e.g., LOX-1 DNA or RNA. Such a ligand can itself be a nucleotide sequence, e.g., a polynucleotide or oligonucleotide, primer or probe, which can be complementary to the biomarker-encoding sequence.

As used herein, the term "antibody" refers to an intact immunoglobulin having two light and two heavy chains or fragments thereof capable of binding to a biomarker protein or a fragment of a biomarker protein. Thus a single isolated antibody or fragment may be a monoclonal antibody, a synthetic antibody, a recombinant antibody, a chimeric antibody, a humanized antibody, a human antibody, or a biospecific antibody or multi-specific construct that can bind two or more target biomarkers. The term "antibody fragment" refers to less than an intact antibody structure, including, without limitation, an isolated single antibody chain, e.g., an scFv fragment, an Fv construct, a Fab construct, an Fc construct, a light chain variable or complementarity determining region (CDR) sequence, etc. For example, a LOX-1 antibody is available from commercial sources, such as Biolegend Inc., San Diego, Calif.

As used herein, "labels" or "reporter molecules" or "detectable label components" are chemical or biochemical moieties useful in association with a ligand, that alone or in concert with other components enable the detection of a target, e.g., the biomarker LOX-1. Such labels or components include, without limitation, fluorescent agents, chemiluminescent agents, chromogenic agents, quenching agents, radionucleotides, enzymes, enzymatic substrates, cofactors, inhibitors, radioactive isotopes, magnetic particles, and other moieties known in the art. In certain embodiment, the "labels" or "reporter molecules" are covalently or noncovalently associated with the ligand. Such labels are capable of generating a measurable signal alone, e.g., radioactivity, or in association with another component, e.g., an enzymatic signal in the presence of a substrate.

By "physical substrate is meant a substrate upon which said polynucleotides or oligonucleotides or ligands are immobilized. The physical substrate can be e.g., a glass slide, a plastic support, or a microchip. The term "microarray" refers to an ordered arrangement of binding/complexing array elements or ligands, e.g. antibodies, probes, etc. on a physical substrate.

By "significant change in expression" is meant an upregulation in the expression level of a nucleic acid sequence, e.g., genes or transcript, encoding a selected biomarker, in comparison to the selected reference standard or control; a downregulation in the expression level of a nucleic acid sequence, e.g., genes or transcript, encoding a selected biomarker, in comparison to the selected reference standard or control; or a combination of a pattern or relative pattern of certain upregulated and/or down regulated biomarker genes. The degree of change in biomarker expression can vary with each individual as stated above for protein biomarkers.

The term "polynucleotide," when used in singular or plural form, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The term "polynucleotide" specifically includes cDNAs. The term includes DNAs (including cDNAs) and RNAs that contain one or more modified bases. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide of less than 20 bases, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

One skilled in the art may readily reproduce the compositions and methods described herein by use of the amino acid sequences of the biomarkers and other molecular forms, which are publicly available from conventional sources.

Throughout this specification, the words "comprise", "comprises", and "comprising" are to be interpreted inclusively rather than exclusively. The words "consist", "consisting", and its variants, are to be interpreted exclusively, rather than inclusively. It should be understood that while various embodiments in the specification are presented using "comprising" language, under various circumstances, a related embodiment is also be described using "consisting of" or "consisting essentially of" language.

The term "a" or "an", refers to one or more, for example, "a biomarker," is understood to represent one or more biomarkers. As such, the terms "a" (or "an"), "one or more," and "at least one" are used interchangeably herein.

As used herein, the term "about" means a variability of 10% from the reference given, unless otherwise specified.

Methods

A method for differentiating polymorphonuclear myeloid derived suppressor cells (PMN-MDSCs) from polymorphonuclear neutrophils (PMNs) or monocytic myeloid derived suppressor cells (M-MDSCs) in a biological sample containing these types of cells involves the following steps. The biological sample, e.g., whole blood or a cell suspension, or a tumor exudate, or tissue, e.g., biopsy material, is contacted with a ligand that specifically binds or forms a complex with LOX-1 receptor on the cell surface. As described in the example below, the ligand is an antibody that binds to LOX-1. Thus by contacting the sample with an anti-LOX-1 antibody, one may detect antibody-conjugate complexes in the sample. However, other ligands can be used in a similar fashion. The resulting complexes of ligand-bound LOX-1-cells in the sample are detected. Such detection can be based upon separation of the ligand-bound cells from unbound cells in the sample. The LOX-1-bound cells are PMN- MDSCs substantially free of PMN. In certain embodiments, the ligand is an anti-LOX-1 antibody, or an anti-LOX-1 antibody fragment. In certain embodiments, the ligands are associated with a detectable label component. In still other embodiments, the ligand is immobilized on a substrate.

In samples containing red blood cells, such as whole blood, one embodiment of the method involves killing or lysing the red blood cells to permit their elimination from the sample and possible interference with the results of the assay. In one aspect, the methods described herein comprise combining the whole blood sample with a lytic reagent system. This step can occur before contact of the sample with the ligand. In another embodiment, this step can occur after contact of the sample with the ligand. In still another embodiment, this step can occur simultaneously or substantially simultaneously with contact with the ligand. In such embodiments, the lytic reagent system is used to lyse red blood cells and to preserve the integrity of the remaining cells in the sample. Exemplary lytic reagents, stabilizing reagents and the method of use have been described, e.g., in U.S. Pat. Nos. 6,573,102 and 6,869,798. Alternatively, the reagent system can also be an isotonic lysing reagent as described in U.S. Pat. No. 5,882,934. Other lytic reagents known in the art can also be used for the purpose of the present methods.

The detection and separation of the ligand bound LOX-1 cells in the sample may be accomplished by a physical characteristic, such as the difference in size or weight of the bound LOX-1 cells vs. the unbound cells which do not have LOX-1 on their surfaces. Such detection and/or separation techniques can thus employ appropriately sized filtration units, or the use of flow cytometry, or chromatographic or centrifugation techniques (size exclusion or weight exclusion), among others known to the art.

Alternatively, where the ligand is associated with a detectable label component, the detection and separation may employ methods of detecting independently detectable labels by radioactivity, light wavelength, etc. Where the ligand is associated with a label which is capable of generating a measurable detectable signal when contacted with another label component, these methods employ the addition of such components and suitable detection methods dependent upon the signal generated. The separated, collected ligand-bound LOX-1$^+$ cells are then collected and counted.

Where the ligand is immobilized on a physical substrate, the separating step can include washing the unbound cells and other debris in the sample from the substrate and counting or collecting the bound PMN-MDSCs from the substrate. In another embodiment, the separating step comprises treating the sample with a reagent, such as an enzymatic substrate, where the label is an enzyme. The interaction of the label and enzymatic substrate or cofactor identifies LOX-1-PMN-MDSC complexes from unbound cells to permit enumeration of PMN-MCSC.

The method of identifying and separating PMN-MDSCs from a sample can also include contacting the biological sample with other biomarkers that identify as a single population both PMN-MDSCs and PMNs and/or M-MDSCs and isolating a cell suspension containing PMN-MDSCs and PMNs (and/or M-MDSCs) prior to, or simultaneously with, contacting the cell suspension with the LOX-1 ligand. In still other embodiments of the methods, the sample may be contacted (with or without RBC lysis) with a LOX-1 ligand and a ligand that identifies neutrophils, i.e., other PMN that are not LOX-1$^+$. In one embodiment, the sample is contacted with a LOX-1 ligand and a CD15 ligand. In still other embodiments of the methods, the sample may be contacted with a LOX-1 ligand and a CD66b ligand. Still other ligands that identify neutrophils generally may be useful in this context.

In one embodiment, therefore, the method involves contacting the biological sample with the ligand for CD15 prior to, or simultaneously with, the use of the LOX-1 ligand. In one embodiment, therefore, the method involves contacting the biological sample with a ligand for CD66b prior to, or simultaneously with, the use of the LOX-1 ligand. In one embodiment, therefore, the method involves contacting the biological sample with a ligand for CD14 prior to, or simultaneously with, the use of the LOX-1 ligand. In one embodiment, therefore, the method involves contacting the biological sample with a ligand for CD11b prior to, or simultaneously with, the use of the LOX-1 ligand. In one embodiment, therefore, the method involves contacting the biological sample with the ligand for CD33, prior to, or simultaneously with, the use of the LOX-1 ligand. In one embodiment, therefore, the method involves contacting the biological sample with a ligand for CD14 and a ligand for CD15 prior to, or simultaneously with, the use of the LOX-1 ligand. In another embodiment, therefore, the method involves contacting the biological sample with a ligand for CD14, and a ligand for CD11b prior to, or simultaneously with, the use of the LOX-1 ligand. In another embodiment, therefore, the method involves contacting the biological sample with a ligand for CD14 and a ligand for CD33 prior to, or simultaneously with, the use of the LOX-1 ligand.

In another embodiment, therefore, the method involves contacting the biological sample a ligand for CD15 and a ligand for CD11b prior to, or simultaneously with, the use of the LOX-1 ligand. In another embodiment, therefore, the method involves contacting the biological sample with a ligand for CD15 and a ligand for CD33 prior to, or simultaneously with, the use of the LOX-1 ligand. In another embodiment, therefore, the method involves contacting the biological sample with a ligand for CD15, a ligand for CD11b and a ligand for CD33 prior to, or simultaneously with, the use of the LOX-1 ligand. In another embodiment, therefore, the method involves contacting the biological sample with a ligand for CD14, a ligand for CD11b and a ligand for CD33 prior to, or simultaneously with, the use of the LOX-1 ligand.

In one embodiment of the method, any of these biomarkers may be detected prior to, or simultaneously with, the detection of the LOX-1 biomarker. The use of these other ligands assists in identifying all PMNs from other cells in the sample. Subsequent exposure of this population of cells from the sample with the LOX-1 ligands enables further separation of the PMN-MDSCs from the PMN population.

In one embodiment, following contact with the LOX-1 ligand and a second neutrophil specific biomarker ligand, such as a CD15 ligand or CD66b ligand, one may calculate the number of LOX-1$^+$ vs. CD15$^+$ or the number of LOX-1$^+$ vs. CD66b$^+$ cells are present in the sample. Such calculation can involve cell counting systems known to those of skill in the art.

In another embodiment, the method involves collecting as a second population, the cells which did not form complexes with the ligands, e.g., are not providing a detectable signal or are not immobilized on the substrate. This second population contains PMNs and other cells substantially free from PMN-MDSCs.

In still another embodiment, the methods described herein permit the obtaining of a population of cells enriched in human polymorphonuclear myeloid derived suppressor cells (PMN-MDSCs) by isolating from a cell suspension those cells which express LOX-1 to provide a population of cells enriched with PMN-MDSCs.

In still another embodiment, the methods involve measuring the amount of soluble LOX-1$^+$ in the serum and correlating that number with the number of LOX-1$^+$ PMN-MDSC.

These methods also permit the removal of human PMN-MDSCs from a cell population, comprising isolating from the cell population those cells which express LOX-1.

These methods are useful in one embodiment for monitoring of the progression or metastasis of a cancer or the monitoring of therapy in a cancer patient by permitting the evaluation of an increase in the LOX-1 cell surface receptor in a biological fluid of a patient having a cancer or under treatment for cancer. The increase of LOX-1+ cell number is indicative of metastasizing cancer or a progression of cancer. In other embodiments, this method may be useful diagnostically to initially detect the presence of cancer.

These methods depend initially upon obtaining an accurate enumeration or concentration of a PMN-MCSC cell population, substantially free of any PMNs, from a suitable biological sample of a subject. In one embodiment, these methods of determining an accurate cell count/concentration of cells expressing LOX-1 in a subject having a cancer or being treated for a cancer can be used to monitor the progression of the cancer (with or without treatment).

In still another embodiment, the use of these methods to determine an accurate measurement of LOX-1$^+$ cells enable the monitoring of metastasis in a cancer, e.g., an increase in the LOX-1$^+$ cell number indicates metastatic cancer. In another embodiment, these methods are useful to monitor and/or influence cancer treatment. For example, where the LOX-1+ cell number is increasing prior to cancer therapy, and subsequent performance of the method on a similar sample in the subject does not show a decrease in LOX-1+ cell number, the method can indicate that a change in therapeutic method or dosage is necessary.

In another embodiment, these methods of determining an accurate cell count/concentration of cells expressing LOX-1 in a subject suspected of having cancer, can diagnose the presence of cancer. In another embodiment, these methods can diagnose the aggressiveness of a cancer. In another embodiment, these methods can diagnose the stage of a cancer. According to the inventors' early studies, in most healthy individuals the proportion of LOX-1$^+$ PMN is less than between 0.5% to 1% PMN. Patients with stage II diseases usually have between about 3 about 5% of LOX-1$^+$ PMN and patients at stages III-IV have over 5% to about 12% PMN.

In still another aspect, the method of measuring the LOX-1$^+$ population in a fluid sample, such as whole blood, can be employed as a research method to determine the cause of the increase in such cells during the progression of a cancer.

Compositions

In yet another embodiment, the methods described above result in a composition of cells, i.e., a substantially pure population of PMN-DMSCs produced by isolating LOX-1$^+$ cells from a biological sample by contacting the sample with a reagent that forms a complex or binds to LOX-1. The methods described above can also result in a population of PMNs which contain substantially no PMN-DMSCs. These cell populations are useful in research.

EXAMPLES

The invention is now described with reference to the following examples. These examples are provided for the purpose of illustration only. The compositions, experimental protocols and methods disclosed and/or claimed herein can be made and executed without undue experimentation in light of the present disclosure. The protocols and methods described in the examples are not considered to be limitations on the scope of the claimed invention. Rather this specification should be construed to encompass any and all variations that become evident as a result of the teaching provided herein. One of skill in the art will understand that changes or variations can be made in the disclosed embodiments of the examples, and expected similar results can be obtained. For example, the substitutions of reagents that are chemically or physiologically related for the reagents described herein are anticipated to produce the same or similar results. All such similar substitutes and modifications are apparent to those skilled in the art and fall within the scope of the invention.

Example 1: Identifying Discriminatory Markers

In order to identify specific markers discriminating between these two populations, we performed genome-wide microarrays (Human HT-12 v4 expression Beadchip, Illumina) to compare the gene expression profiles between PMN-MDSC and PMN from the same cancer patients (7 patients) as well as age matching healthy donors (4 donors). All samples of peripheral blood (PB) were collected from patients at the Helen F. Graham Cancer Center and were analyzed within 3 hours of collection. PMN-MDSCs were evaluated in mononuclear fraction of PB after ficoll density gradient. PMN were evaluated from the cell fraction remaining after removal of mononuclear cells. Cells were resuspended in PBS and loaded on a step density gradient (Percoll 63% on top of Percoll 72%) to separate PMNs in a monolayer between the two Percoll phases. In an attempt to minimize the number of potential candidates and to identify true marker of PMN-MDSC, we analyzed the gene expression profiles of PMN-MDSC from head and neck cancer patients (4 samples) as well as lung cancer patients (3 samples).

The analysis was performed using SAM analysis (significant analysis of microarray) and the false discovery rate set at 5% (analysis was performed by the Wistar bioinformatics core facility). This analysis allowed us to identify more than 1500 genes showing a significant differential expression between PMN-MDSC and PMN. Interestingly, the vast majority of the differentially regulated genes were up-regulated in PMN-MDSC compared to PMN. After filtering for molecules expressed on the surface of the cells, we ended with a relatively small list of specific biomarkers for PMN-MDSC. One of these biomarkers is the Lectin-like oxidized low-density lipoprotein receptor-1 (LOX-1), a 50 kDa transmembrane glycoprotein encoded by the gene olr1 (oxidized LDL receptor 1). According to the microarray, LOX-1 was increased by 5.75 fold in PMN-MDSC compared to PMN.

Example 2—Confirming Validity of LOX-1 as a Biomarker

To confirm the validity of LOX-1 as a potential biomarker of PMN-MDSC, we analyzed the expression of this receptor by flow cytometry using an anti-LOX-1 monoclonal antibody (clone 15C4; Biolegend Inc., San Diego, Calif.) in blood samples from patients with 4 different types of cancer: head and neck, breast, non-small lung, or colon cancer.

We first analyzed the expression of LOX-1 using the classical definitions of PMN-MDSC (CD11b$^+$ CD14$^-$ CD15+ and CD33+ from the low density mononuclear cells fraction) and PMN (cells with the same phenotype from high density fraction). The results of this experiment are reported graphically when healthy donors (HD) were compared with all cancer patients in FIG. 1. About 30% of the PMN-MDSC from all cancer patients (n=23) was found to express LOX-1 on their surface compared to less than 3% of the PMN from matching patients or about 1% from PMN from healthy donor (n=9) (p<0.001).

The results of this experiment are reported by separating the results for cancer types as shown in the graphs of FIGS. 2A through 2D. The results in all 4 types of cancer were similar.

Figure 3:
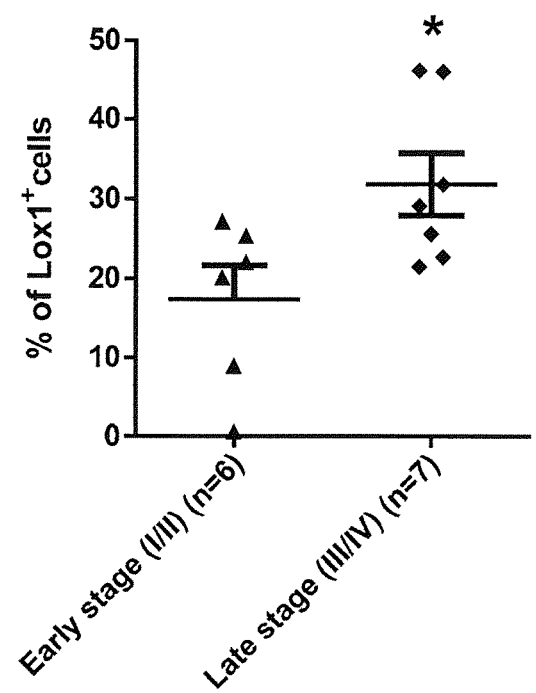
FIG. 3 is a graph showing the link between the proportion of LOX-1⁺ cells among PMN-MDSC in 6 early stage (I or II, ▲) cancer patients and 7 late stage (III or IV, ♦) cancer patients. The data is reported as in FIG. 1 but separated based on the stage of cancers. *-p<0.05 between patients with early and late stages of the diseases.

Preliminary data also suggest that the percentage of PMN-MDSC expressing LOX-1 could correlate with the stage of the disease. As shown graphically in the preliminary analysis of FIG. 3, only 20% of the PMN-MDSC from samples from early stage cancer patients expresses LOX-1 in comparison to 32% in samples from late stage cancer patients (p<0.05).

Example 3—Analysis of Whole Blood Samples

We also performed an analysis of unseparated whole blood samples. As shown in FIGS. 4A and 4C, as expected, about 1% or less of the CD11b+ CD14− CD15+ and CD33+ PMN from healthy donors expressed LOX-1 on their surface. However, in samples from cancer patients (both head and neck and lung cancer patients), almost 5% of the PMN types of cells exhibit a positive staining for LOX-1 (≈2.3% of the total leukocytes) strongly supporting the designation of LOX-1 as a specific marker of PMN-MDSC. These results were confirmed by analyzing the disease separately, as reported in FIGS. 4B and 4D.

Example 4—Stimulation of T-Cell Proliferation

Figure 5A:
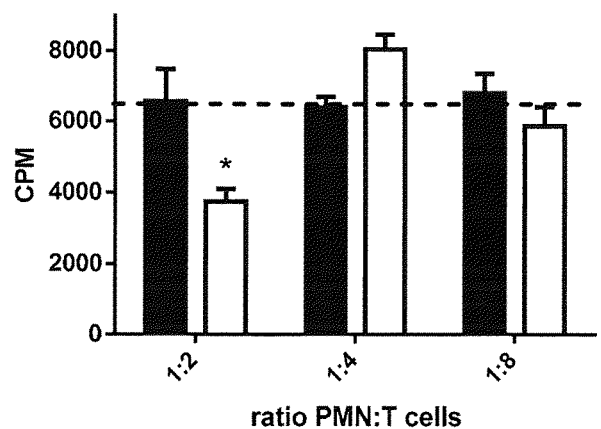
FIG. 5A is a bar graph showing that LOX-1⁺ PMN from cancer patient No. 1 suppresses T cell function. Samples of whole blood were collected from patient with HNC. Red cells were lysed, and PMN were highly enriched by negative selection using Miltenyi bead kit (MACSxpress Neutrophil isolation kit). Cells were then labeled with PE-conjugated LOX-1 antibody followed by anti-PE beads. LOX-1⁺ and LOX-1⁻ PMN were added to mixed allogeneic reaction at indicated ratios and T-cell proliferation was (for LOX-1⁻ PMN, black bar; for LOX-1+ PMN, white bar) measured 5 days later by ³H-thymidin uptake. Each experiment was performed in triplicate. Dashed line—the level of T cell proliferation in the absence of PMN. *-p<0.05 difference from control and from between the group in FIG. 5B and FIG. 5C.
Figure 5B:
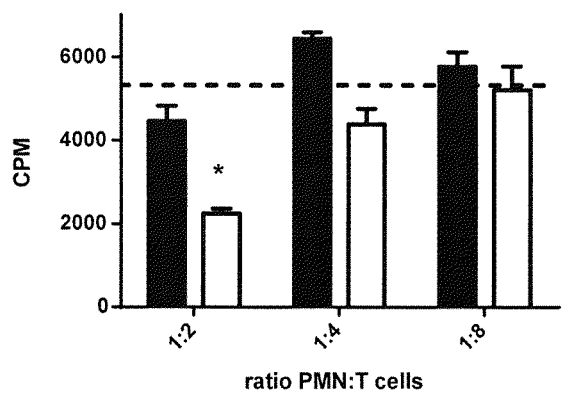
FIG. 5B shows a bar graph for Patient #2 in the experiment described in FIG. 5A using the same symbols.
Figure 5C:
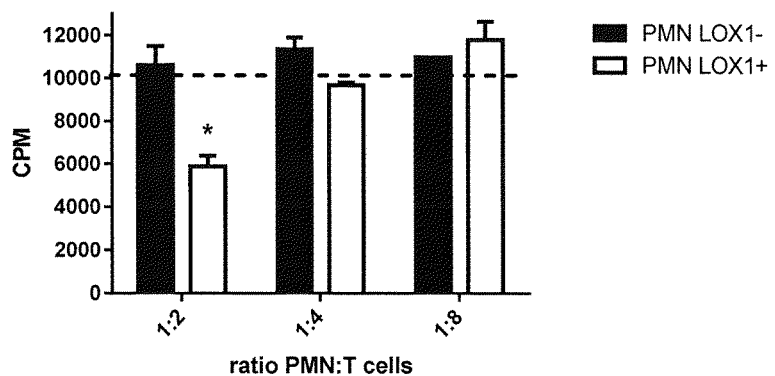
FIG. 5C shows a bar graph for Patient #3 in the experiment described in FIG. 5A using the same symbols.

To assess possible functional relevance of these findings, LOX-1+ and LOX-1− PMN were isolated from peripheral blood of three patients with head and neck cancer using magnetic beads separation as follows: Samples of whole blood were collected from patient with HNC. Red cells were lysed, and PMN were highly enriched by negative selection using Mitlenyi bead kit. Cells were then labeled with biotinylated LOX-1 antibody followed by streptavidin beads. LOX-1+ and LOX-1− PMN were added to mixed allogeneic reaction at ratios if 1:2, 1:4 and 1:8, and T-cell proliferation was measured 5 days later by $^3$H-thymidin uptake. Experiments were performed in triplicate. Cells were used in allogeneic mixed leukocyte reactions where dendritic cells from healthy donors were cultured with T cells from unrelated healthy donors. Mixing cells from unrelated donors stimulated potent T-cell proliferation. As in shown in FIGS. 5A through 5C, the addition of LOX-1− PMN did not affect T-cell proliferation, whereas LOX-1+ PMN potently suppress T-cell response.

Example 5—Evaluation of ROS

Reactive oxygen species (ROS) are considered as major mechanism responsible for immune suppressive activity of PMN-MDSC. We evaluated the level of ROS in LOX-1+ and LOX-1− PMN in patients with head and neck cancers (HNC) as follows. Samples of whole blood were collected from head and neck cancer patients. Red cells were lysed and PMN were labeled with CD15, LOX-1 antibodies, and with the cell permeant reagent 2',7'-dichlorofluorescin diacetate (DCFDA). DCFDA is a fluorogenic dye that measures hydroxyl, peroxyl and other reactive oxygen species (ROS) activity within the cell. After diffusion in to the cell, DCFDA is deacetylated by cellular esterases to a non-fluorescent compound, which is later oxidized by ROS into 2',7'-dichlorofluorescein (DCF). DCF is a highly fluorescent compound which can be detected by fluorescence spectroscopy with maximum excitation and emission spectra of 495 nm and 529 nm respectively.

As shown in the histograms of FIGS. 6A-6D, LOX-1+ PMN had almost two-fold higher amount of ROS than LOX-1− PMN.

Example 6—Correlation of Soluble LOX-1 with PMN-MDSC

Figure 7A:
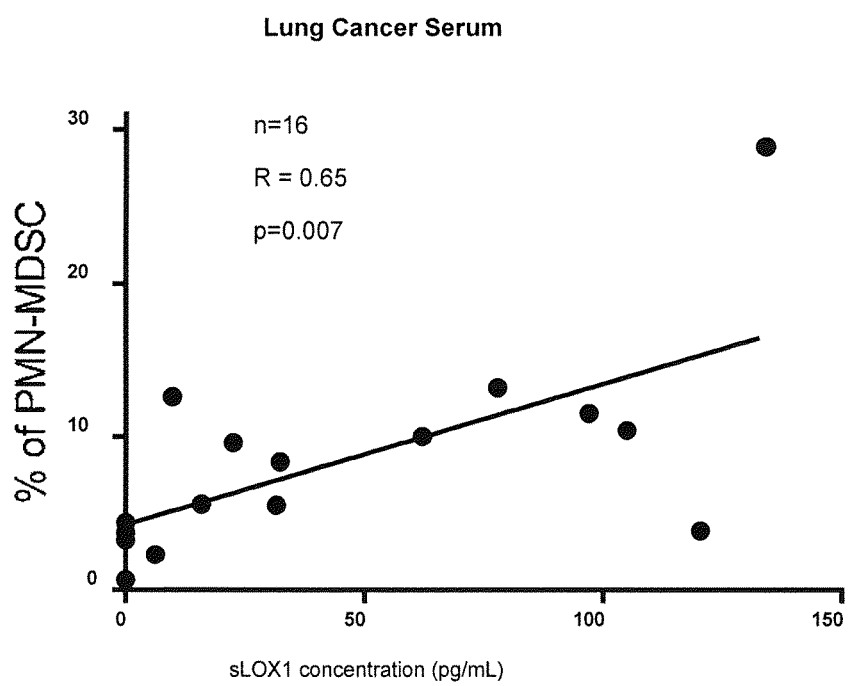
FIG. 7A shows the correlation between the presence of PMN-MDSC and soluble LOX-1 in sera of 16 lung cancer patients. Concentration of sLOX-1 was measured in sera using ELISA. Proportion of PMN-MDSC was measured as described in FIGS. 2A-2D. R=correlation coefficient Pearson. N=number of pairs analyzed.
Figure 7B:
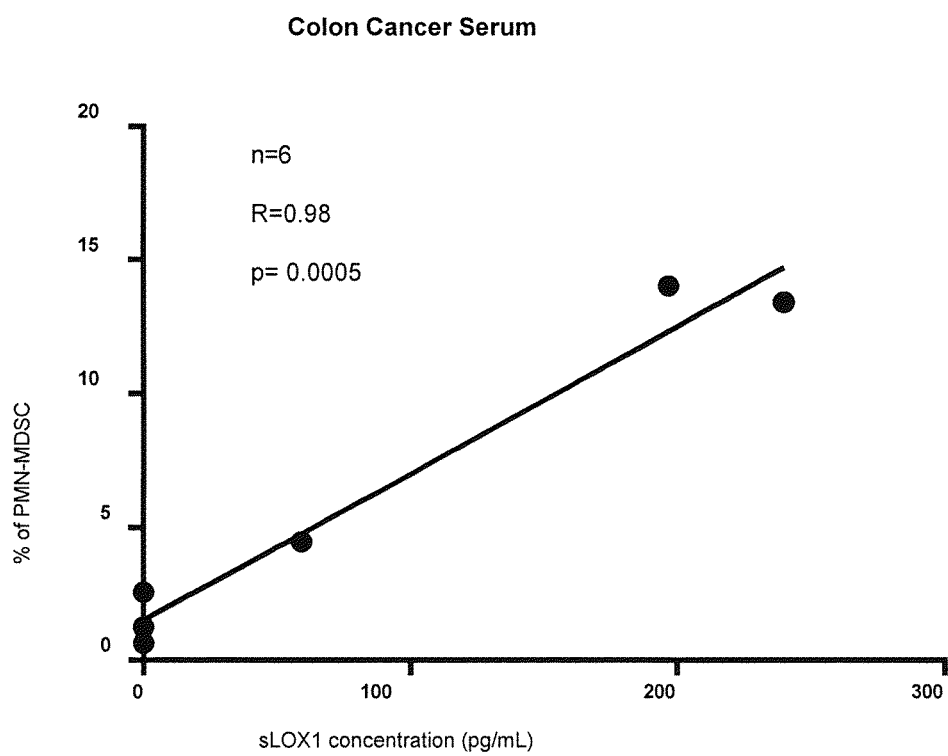
FIG. 7B shows the correlation between the presence of PMN-MDSC and soluble LOX-1 in sera of 6 colon cancer patients. Concentration of soluble LOX-1 (sLOX-1) was measured in sera using ELISA. Proportion of PMN-MDSC was measured as described in FIGS. 2A-2D. R=correlation coefficient Pearson. N=number of pairs analyzed.

LOX-1 is known to be cleaved from the surface of the cells and can be detected in sera of patients. We hypothesized that LOX-1 may be cleaved from PMN-MDSC and therefore, the presence of soluble LOX-1 (sLOX-1) may correlate with the amount of LOX-1+ PMN-MDSC. Concentrations of sLOX-1 were measured in sera of 16 lung cancer patients and 6 colon cancer patients using ELISA. Samples of whole blood were collected; PBMC were purified using Ficoll gradient; and the proportion of PMN-MDSC out of total live PBMC was measured by flow cytometry using antibodies to CD11b, CD33, CD14, and CD15. The correlation between the presence of PMN-MDSC and soluble LOX-1 in sera of the lung cancer patients is shown in FIG. 7A and for colon cancer patients in FIG. 7B.

Highly significant correlation between these two parameters was found (correlation of coefficient in lung cancer patients 0.65, p=0.007; in patients with colon cancer 0.98, p=0.0005).

Each and every patent, patent application US provisional patent application Nos. 62/187,991 filed Jul. 2, 2015 and 62/169,368 filed Jun. 1, 2015, and any document listed herein, and the sequence of any publically available nucleic acid and/or peptide sequence cited throughout the disclosure, is expressly incorporated herein by reference in its entirety. Embodiments and variations of this invention other than those specifically disclosed above may be devised by others skilled in the art without departing from the true spirit and scope of the invention. The appended claims include such embodiments and equivalent variations.

REFERENCES

1. Talmadge, J. E. & Gabrilovich, D. I. 2013 History of myeloid-derived suppressor cells. Nat Rev Cancer 13, 739-752
2. Gabrilovich, D. I. & Nagaraj, S. 2009 Myeloid-derived suppressor cells as regulators of the immune system. Nat Rev Immunol 9, 162-174
3. Gabrilovich, D. I et al. 2012 Coordinated regulation of myeloid cells by tumours. Nat Rev Immunol 12, 253-268 (2012).
4. Montero, A. J., et al. 2012 Myeloid-derived suppressor cells in cancer patients: a clinical perspective J Immunother 35, 107-115
5. Gabrilovich, D. I., et al. 2012 Coordinated regulation of myeloid cells by tumours. Nat Rev Immunol 12, 253-268
6. Youn, J. I. et al. 2008 Subsets of myeloid-derived suppressor cells in tumor-bearing mice. J Immunol 181, 5791-5802

7. Filipazzi, P., et al. 2007 Identification of a new subset of myeloid suppressor cells in peripheral blood of melanoma patients with modulation by a granulocyte-macrophage colony-stimulation factor-based antitumor vaccine. J Clin Oncol 25, 2546-2553
8. Poschke, I. & Kiessling, R. 2012 On the armament and appearances of human myeloid-derived suppressor cells. Clinical immunology 144, 250-268
9. Youn, J. I., et al., 2012 Characterization of the nature of granulocytic myeloid-derived suppressor cells in tumor-bearing mice. J Leukoc Biol 91, 167-181
10. Sawamura, T., et al. 1997 An endothelial receptor for oxidized low-density lipoprotein. Nature 386, 73-77
11. Taye, A. & El-Sheikh, A. A. 2013 Lectin-like oxidized low-density lipoprotein receptor 1 pathways. Eur J Clin Invest 43, 740-745
12. Pirillo, A., et al. 2013 LOX-1, OxLDL, and atherosclerosis. Mediators Inflamm 2013, 152786
13. Lu, J. et al. 2011 Oxidative stress and lectin-like ox-LDL-receptor LOX-1 in atherogenesis and tumorigenesis. Antioxid Redox Signal 15, 2301-2333
14. Hirsch, H. A., et al. 2010 A transcriptional signature and common gene networks link cancer with lipid metabolism and diverse human diseases. Cancer Cell 17, 348-361

The invention claimed is:

1. A method of obtaining a population of cells enriched in human polymorphonuclear myeloid derived suppressor cells (PMN-MDSCs) comprising contacting a biological sample from a human cancer patient that contains both PMN-MDSCs and polymorphonuclear neutrophils (PMN) with an antibody that binds to LOX-1 and separating antibody-bound PMN-MDSC from PMN that are not bound to the antibody, wherein the antibody-bound portion of the sample are a population of cells enriched with PMN-MDSCs and substantially depleted of PMN.

2. The method according to claim 1, wherein said anti-LOX-1 antibody is an scFv fragment, optionally associated with a detectable label component.

3. The method according to claim 1, wherein the antibody is immobilized on a substrate.

4. The method according to claim 1, wherein the antibody is associated with a detectable label component.

5. The method according to claim 4, wherein the detectable label component is independently detectable or is capable of generating a measurable detectable signal when contacted with another label component.

6. The method according to claim 1, wherein the separating step comprises washing the unbound cells and other debris in the sample from the substrate and counting or collecting the bound PMN-MDSCs from the substrate.

7. The method according to claim 1, wherein the separating step comprises treating the sample with a reagent which identifies LOX-1$^+$-PMN-MDSC complexes from unbound cells to permit enumeration of PMN-MCSC.

8. The method according to claim 1, wherein the biological fluid sample is whole blood and wherein the method further comprises destroying or lysing any red blood cells in the sample.

9. The method according to claim 1, wherein the biological sample is a circulating tumor cell or fluids containing them or a tissue or tissue extract containing the PMN-MDSC.

* * * * *

UNITED STATES PATENT AND TRADEMARK OFFICE
CERTIFICATE OF CORRECTION

| | |
|---|---|
| PATENT NO. | : 11,073,521 B2 |
| APPLICATION NO. | : 15/577922 |
| DATED | : July 27, 2021 |
| INVENTOR(S) | : Gabrilovich et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 420 days.

Signed and Sealed this
Tenth Day of January, 2023

Katherine Kelly Vidal
*Director of the United States Patent and Trademark Office*